(12) United States Patent
Kawata et al.

(10) Patent No.: US 7,294,121 B2
(45) Date of Patent: Nov. 13, 2007

(54) DISPOSABLE BODY FLUID ABSORBENT PAD

(75) Inventors: Hikari Kawata, Kagawa-ken (JP);
Masashi Nakashita, Kagawa-ken (JP);
Kaori Yamauchi, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

(21) Appl. No.: 11/327,602

(22) Filed: Jan. 6, 2006

(65) Prior Publication Data

US 2006/0111685 A1 May 25, 2006

Related U.S. Application Data

(62) Division of application No. 10/670,019, filed on Sep. 24, 2003.

(30) Foreign Application Priority Data

Sep. 30, 2002 (JP) ............................ 2002-285937
Apr. 30, 2003 (JP) ............................ 2003-125111

(51) Int. Cl.
*A61F 13/15* (2006.01)
(52) U.S. Cl. ........................... 604/385.19; 604/385.14; 604/385.13; 604/385.24; 604/385.25; 604/385.27; 604/385.28; 604/385.29; 604/385.3
(58) Field of Classification Search .......... 604/385.01, 604/385.19, 385.24, 385.201, 385.14, 385.13, 604/385.25, 385.27, 385.28, 385.29, 385.3
See application file for complete search history.

(56) References Cited

U.S. PATENT DOCUMENTS

| | | | |
|---|---|---|---|
| 3,369,545 A | 2/1968 | Wanberg | |
| 4,085,753 A | 4/1978 | Gellert | |
| 4,372,309 A | 2/1983 | Fowler | |
| 4,493,713 A | 1/1985 | Izzo | |
| 4,507,121 A | 3/1985 | Leung | |
| 4,551,145 A | 11/1985 | Ryan | |
| 4,923,455 A | 5/1990 | Dean et al. | |

(Continued)

FOREIGN PATENT DOCUMENTS

JP 2002-119528 4/2002

(Continued)

OTHER PUBLICATIONS

Patent Abstracts of Japan, vol. 2002, No. 08, Aug. 5, 2002 & JP 2002 119528 A (Hamada Koichi) Apr. 23, 2002.

*Primary Examiner*—Jaccqueline F. Stephens
(74) *Attorney, Agent, or Firm*—Butzel Long

(57) ABSTRACT

Here is disclosed a pad being relatively large in its longitudinal direction and comprising a liquid-pervious topsheet, a liquid-impervious backsheet, a liquid-absorbent core interposed between these top- and backsheets and an cover sheet lying outside the backsheet and extending from an intermediate region to a rear region of the pad. The cover sheet has fixed side edge portions fixed to transversely opposite side edges of the pad, a fixed end portion fixed to a rear end portion of the pad and a free portion extending between the fixed side edge portions and the fixed end portion and let free from the pad so that a pocket opening from the side of the front region toward the side of the rear region is defined between the backsheet and the cover sheet.

6 Claims, 15 Drawing Sheets

U.S. PATENT DOCUMENTS

| | | |
|---|---|---|
| 4,931,052 A | 6/1990 | Feldman |
| 5,071,414 A | 12/1991 | Elliott |
| 5,141,505 A | 8/1992 | Barrett |
| D343,233 S | 1/1994 | Lanmon et al. |
| 5,643,189 A | 7/1997 | Masini |
| 5,760,694 A | 6/1998 | Nissim et al. |
| 5,778,110 A | 7/1998 | Furuya |
| 6,254,583 B1 * | 7/2001 | Coates .................. 604/385.14 |
| 6,454,748 B1 | 9/2002 | Ives |
| 6,475,204 B1 | 11/2002 | Walker |
| 6,558,499 B1 | 5/2003 | Pargass et al. |
| 6,599,262 B1 | 7/2003 | Masini |
| 6,617,488 B1 | 9/2003 | Springer et al. |
| 6,911,022 B2 | 6/2005 | Steger et al. |
| 6,953,451 B2 * | 10/2005 | Berba et al. ........... 604/385.01 |
| 2002/0091368 A1 | 7/2002 | LaVon et al. |

FOREIGN PATENT DOCUMENTS

| | | |
|---|---|---|
| WO | WO 02 094156 | 11/2002 |

* cited by examiner

DISPOSABLE BODY FLUID ABSORBENT PAD

RELATED APPLICATION

This application is a divisional application of U.S. patent application Ser. No. 10/670,019, filed Sep. 24, 2003 to which priority is claimed under 35 U.S.C. §120 and though which priority is claimed under 35 U.S.C. §119 to Japanese Patent Application No. 2002-285937, filed Sep. 30, 2003.

BACKGROUND OF THE INVENTION

The present invention relates to a disposable body fluid absorbent pad.

Japanese Patent Application Publication No. 2002-119528A discloses a disposable body fluid absorbent pad being relatively large in a longitudinal direction in which the pad defines front and rear regions and an intermediate region extending between these front and rear regions in the longitudinal direction, the pad comprises a liquid-pervious topsheet facing the wearer's body, a liquid-impervious backsheet facing away from the wearer's body and a liquid-absorbent core interposed between these top- and backsheets and extending between these front and rear region, and the pad is contoured by longitudinally opposite end portions extending in a transverse direction outside longitudinally opposite ends of the liquid-absorbent core and transversely opposite side edge portions extending in the longitudinal direction outside transversely opposite side edges of the liquid-absorbent core.

The pad disclosed in the above-cited Publication is provided on the backsheet with loop-like fine rubber members. These rubber members are provided in a transversely middle zone in the intermediate region of the pad. Each of these rubber members has its longitudinally opposite end portions secured to the outer surface of the backsheet and its intermediate portion extending between these end portions is not secured to the backsheet and let free therefrom. In actual use, this pad is placed on the inner surface of shorts which are then put on the wearer's body. The rubber members attached to the backsheet come in contact with the inner surface of the shorts and function as an anti-slip means adapted to prevent the pad from shifting relative to the shorts.

The pad disclosed in the above-cited Publication must rely upon the shorts to wear the pad and can not be used independently. In addition, this pad is merely placed upon the pants and not adapted to bring itself in close contact with the wearer's body, so the shorts must be carefully put on the wearer's body to hold the pad in contact with the wearer's body. Slip down of the shorts from the wearer's crotch region causes the pad to slip off from the wearer's crotch region. In consequence, it is no more possible for the pad to absorb body fluids.

SUMMARY OF THE INVENTION

It is an object of the present invention to provide a disposable body fluid absorbent pad improved so that the pad can be brought in close contact with the wearer's body without relying upon the shorts.

According to the present invention, there is provided a disposable body fluid absorbent pad having a longitudinal direction and a transverse direction, the pad further comprising: a front region; a rear region; an intermediate region between the front region and the rear region; a liquid-pervious topsheet; a liquid-impervious backsheet; a liquid-absorbent core between the liquid-pervious topsheet and the liquid-impervious backsheet; the pad being contoured by longitudinally opposite end portions extending in the transverse direction outside longitudinal front and rear ends of the liquid-absorbent core and transversely opposite side edge portions extending in the longitudinal direction outside transversely opposite side edges of the liquid-absorbent core; and an insertion space means comprising a cover sheet which defines an insertion space between the cover sheet and a part of an outer surface of the liquid-impervious backsheet and at least one opening to guide a wearer's hand into the insertion space, with at least a part of a periphery of the cover sheet joined onto an outer surface of the liquid-impervious backsheet.

The present invention includes the following embodiments.

The cover sheet is superposed over the front, intermediate and rear regions, at least over the intermediate region.

The cover sheet extends at least over the intermediate region and the rear region and has a fixed end portion extending in the transverse direction along the longitudinally rear end portion of the pad, the insertion space defines a pocket opening from the side of the front region toward the side of the rear region.

Elastically members are attached to the front and rear regions and the intermediate region, at least to the intermediate region so as to extend in the longitudinal direction along the opposite side edge portions of the pad and to be contractible in the longitudinal direction.

The longitudinally front and rear end portions of the pad extend inward in the longitudinal direction from the longitudinally front and rear opposite ends of the liquid-absorbent core so as to lie above the liquid-absorbent core while the side edge portions of the pad extend inward in the transverse direction from the opposite side edge portions of the pad so as to lie above the liquid-absorbent core and the longitudinally front and rear end portions cooperate with the side edge portions to form a peripheral wall adapted to surround the liquid-absorbent core.

The peripheral wall is provided with elastically stretchable members attached thereto so that the elastically stretchable members substantially describe loops in a circumferential direction of the peripheral wall and are contractible in the circumferential direction.

A prominence dimension of the liquid-absorbent core measured upward from a surface of the core facing a wearer's body in the front region and a front half of the intermediate region is larger than that in a rear half of the intermediate region and the rear region.

The intermediate region is formed with a folding guide extending across the intermediate region in the transverse direction along which the pad is folded in two with the topsheet inside and the liquid-absorbent core has a stiffness lower in the folding guide than in the other zone of the liquid-absorbent core.

The intermediate region is formed with a folding guide extending across the intermediate region in the transverse direction along which the pad is folded in two with the topsheet inside and the folding guide is formed by the top- and backsheets except for the liquid-absorbent core.

The the liquid-absorbent core is formed in a vicinity of a peripheral edge of the cover sheet with a raised ridge and the liquid-absorbent core has a thickness dimension measured between the top- and backsheets is larger in the raised ridge than in the other zone of the liquid-absorbent core except for the raised ridge.

The cover sheet is colored differently from the top- and backsheets.

The cover sheet has a predetermined indicator element thereon.

DETAILED DESCRIPTION OF THE PREFERRED EMBODIMENTS

Details of the body fluid absorbent pad according to the present invention will be more fully understood from the description given hereunder with reference to the accompanying drawings.

Figure 1:
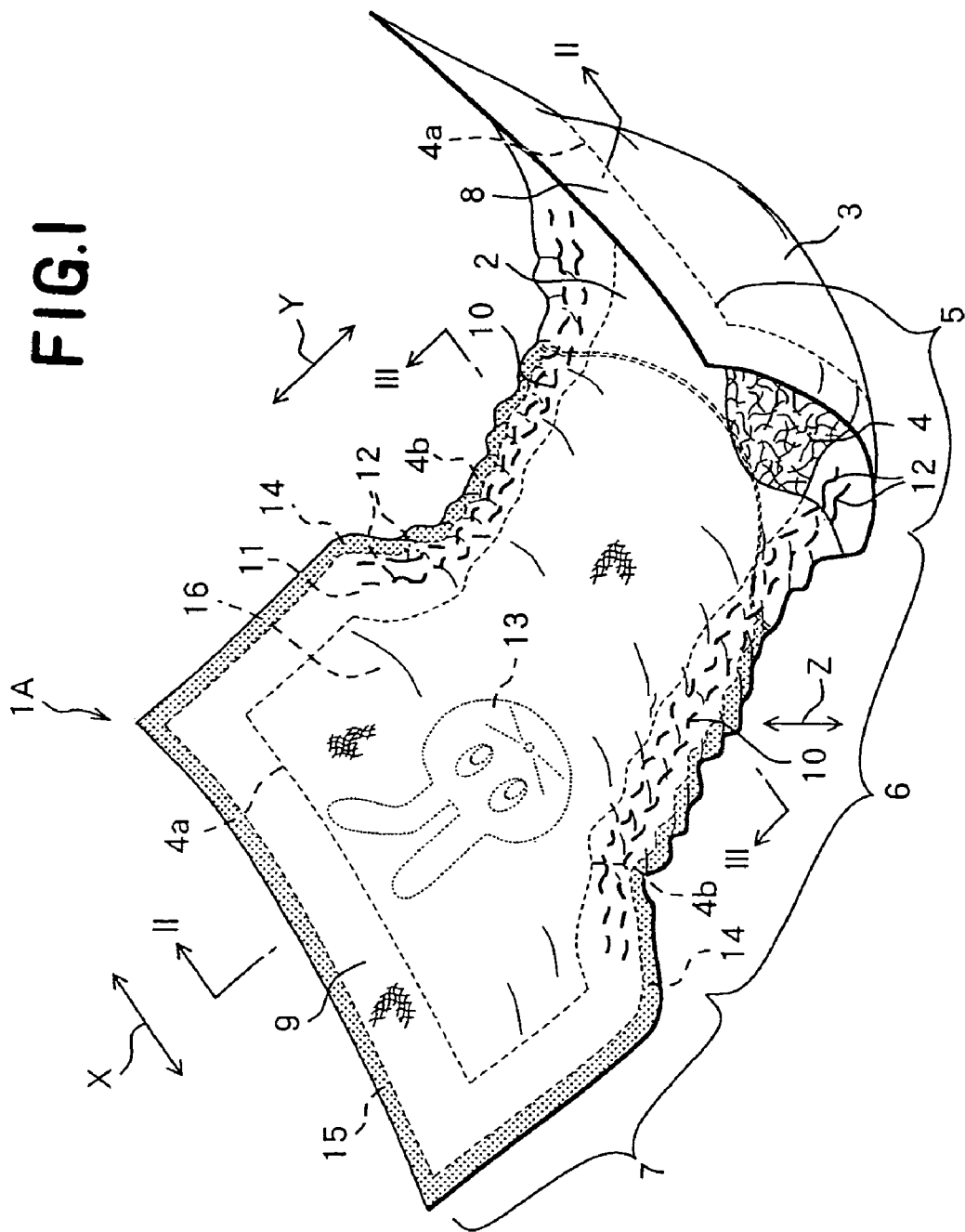
FIG. 1 is a partially cutaway perspective view showing a typical embodiment of a body fluid absorbent pad according to the invention.
Figure 2:
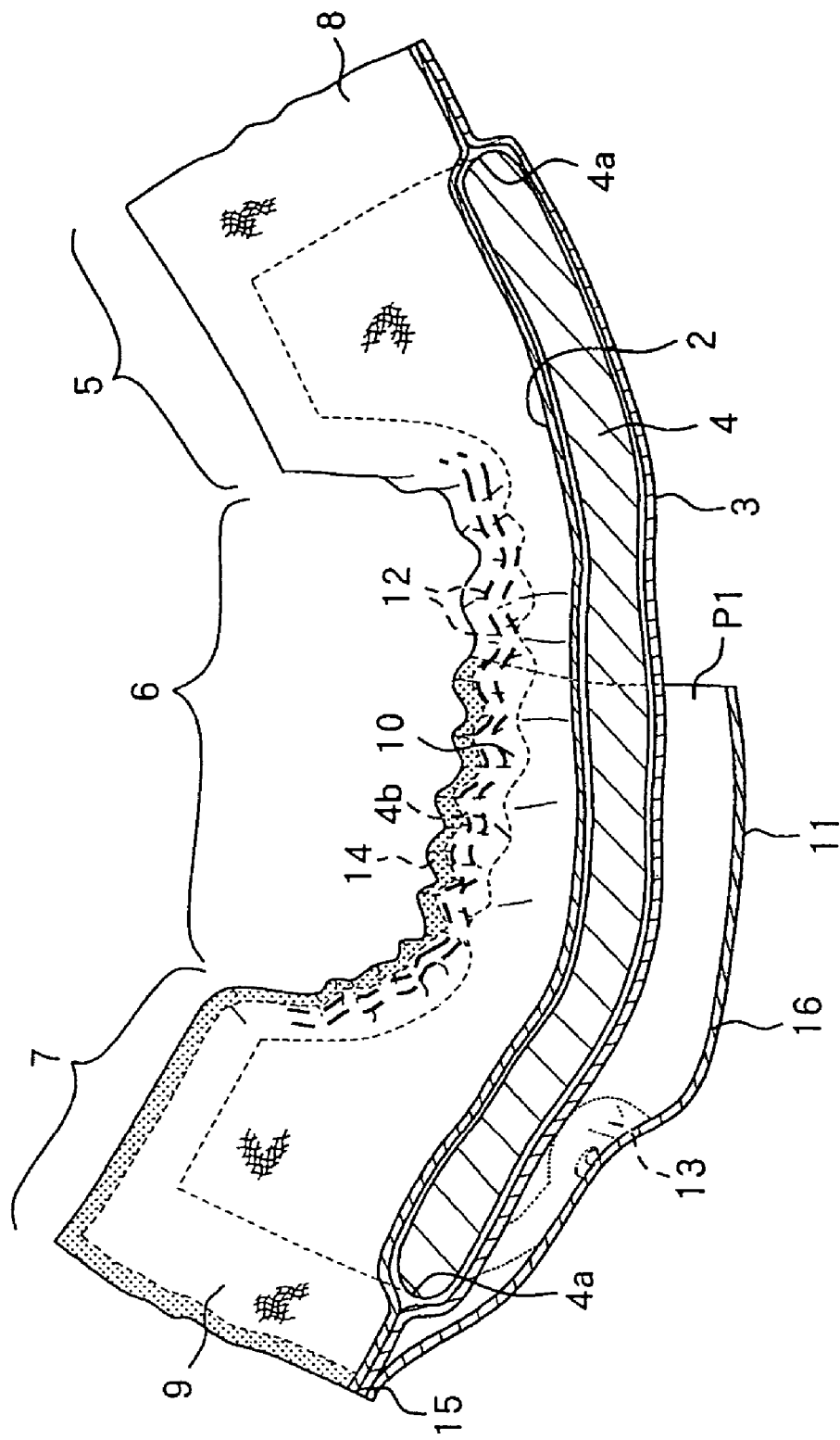
FIG. 2 is a sectional view taken along a line II-II in FIG. 1.
Figure 3:
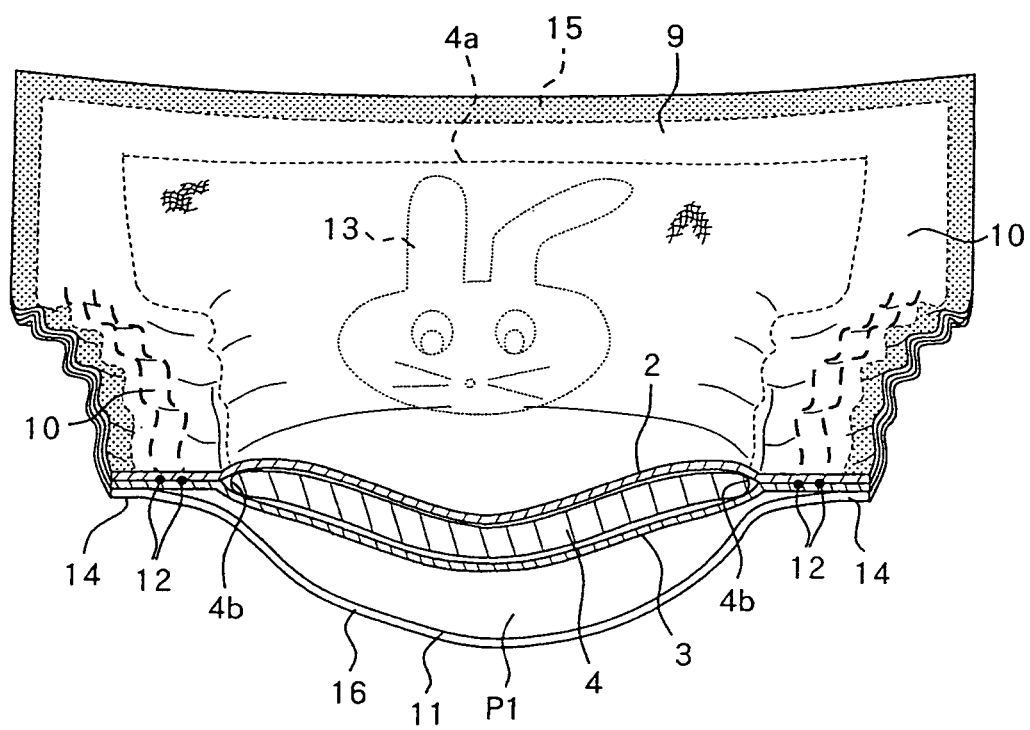
FIG. 3 is a sectional view taken along a line III-III in FIG. 1.

FIG. 1 is a partially cutaway perspective view showing a body fluid absorbent pad 1A as a typical embodiment of the invention, FIG. 2 is a sectional view taken along a line II-II in FIG. 1 and FIG. 3 is a sectional view taken along a line III-III in FIG. 1. In FIG. 1, a transverse direction is indicated by an arrow X, a longitudinal direction is indicated by an arrow Y and a thickness direction is indicated by an arrow Z. Terms used herein "inner surfaces" of top- and backsheets 2, 3 and an cover sheet 11 refer to the surfaces of these sheets 2, 3, 11 facing a core 4 and terms used herein "outer surfaces" of these sheets 2, 3, 11 refer to the surfaces facing away from the core 4.

The pad 1A comprises a liquid-pervious topsheet 2 facing a wearer's body, a liquid-impervious backsheet 3 facing away from the wearer's body and the liquid-absorbent core 4 interposed between the top- and backsheets 2, 3. The pad 1A presents a substantially rectangular shape having a relatively large dimension in the longitudinal direction and defines, in the longitudinal direction, a front region 5, a rear region 7 and an intermediate region 6 extending between the front and rear regions 5, 7. The pad 1A is contoured by front and rear end portions 8, 9 lying outside longitudinally opposite ends 4a of the core 4 so as to extend in the transverse direction and transversely opposite side edge portions 10 lying outside transversely opposite side edges 4b of the core 4 so as to extend in the longitudinal direction. The pad 1A includes the cover sheet 11 lying outside the backsheet 3 and thereby covers the outer surface of the sheet 3.

The core 4 extends between the front and rear regions 5, 7 of the pad 1A and is secured to respective inner surfaces of the top- and backsheets 2, 3. The core 4 comprises a mixture of fluff pulp and super-absorbent polymer or a mixture of fluff pulp, super-absorbent polymer and thermoplastic synthetic resin fiber, in both cases, compressed to a desired thickness. Correspondingly, the core 4 has a stiffness higher than those of the top- and backsheets 2, 3. Preferably the core 4 is entirely wrapped with a liquid-pervious sheet such as a tissue paper or a hydrophilic fibrous nonwoven fabric in order to prevent the core 4 from getting out of its desired shape.

The intermediate region 6 is provided with a plurality of elastically stretchable members 12 which are attached to the side edges 10 in a stretched state so as to extend in the longitudinal direction. These elastic members 12 are interposed between the top- and backsheets 2, 3 and secured to the respective inner surfaces of these sheets 2, 3. Alternatively, these elastic members 12 may extend not only over the intermediate region 6 but also further extend into the front and rear regions 5, 7. In FIG. 1, the pad 1A is curved in the longitudinal direction with the topsheet 2 inside as the elastic members 12 contract inward in the longitudinal direction.

The cover sheet 11 extends over the intermediate region 6 and further over the rear region 7 to the rear end portion 9 of the pad 1A. The cover sheet 11 is formed by substantially non-stretchable hydrophobic fibrous nonwoven fabric. It should be understood that the cover sheet 11 may extend entirely over the front region 5, the intermediate region 6 and the rear region 7. The cover sheet 11 is colored differently from the top- and backsheets 2, 3 (coloration is not shown). For example, in contrast to the creamy white top- and backsheets 2, 3, the cover sheet 11 may be colored in red, blue or yellow. The cover sheet 11 is formed with a predetermined indicator element 13 which is, in this embodiment, illustration of rabbit's head printed on the outer surface of the cover sheet 11. The indicator element 13 is not limited to such an illustration and may be in form of letters, patterns or symbols.

The cover sheet 11 has transversely opposite fixed side edge portions 14 secured to the side edge portions 10 of the pad 1A, a fixed end portion 15 secured to the rear end portion 9 of the pad 1A and a free portion 16 extending between these fixed side edge portions 14 and the fixed end portion 15. Along the fixed side edge portions 14 and the fixed end portion 15, the inner surface of the cover sheet 11 is secured to the outer surface of the backsheet 3. The free portion 16 is not secured to the backsheet 3 and let free therefrom. Between the backsheet 3 and the free portion 16 of the cover sheet 11, a pocket P1 (insertion space) is defined so as to be opened from the side of the front region 5 toward the side of the rear region 7 (See FIGS. 2 and 3). The pocket P1 defines a space into which a wearer 20 of the pad 1A can insert his or her hand 21 as will be described later more in detail.

The front and rear end portions 8, 9 are defined by portions of the top- and backsheets 2, 3 extending outward beyond the longitudinally opposite ends 4a of the core 4 in the longitudinal direction. The top- and backsheets 2, 3 are overlaid and joined together along the front and rear end portions 8, 9. The side edge portions 10 are defined by portions of the top- and backsheets 2, 3 extending outward beyond the transversely opposite side edges 4b of the core 4 in the in the transverse direction. The top- and backsheets 2, 3 are overlaid and joined together along the side edge portions 10.

Figure 4:
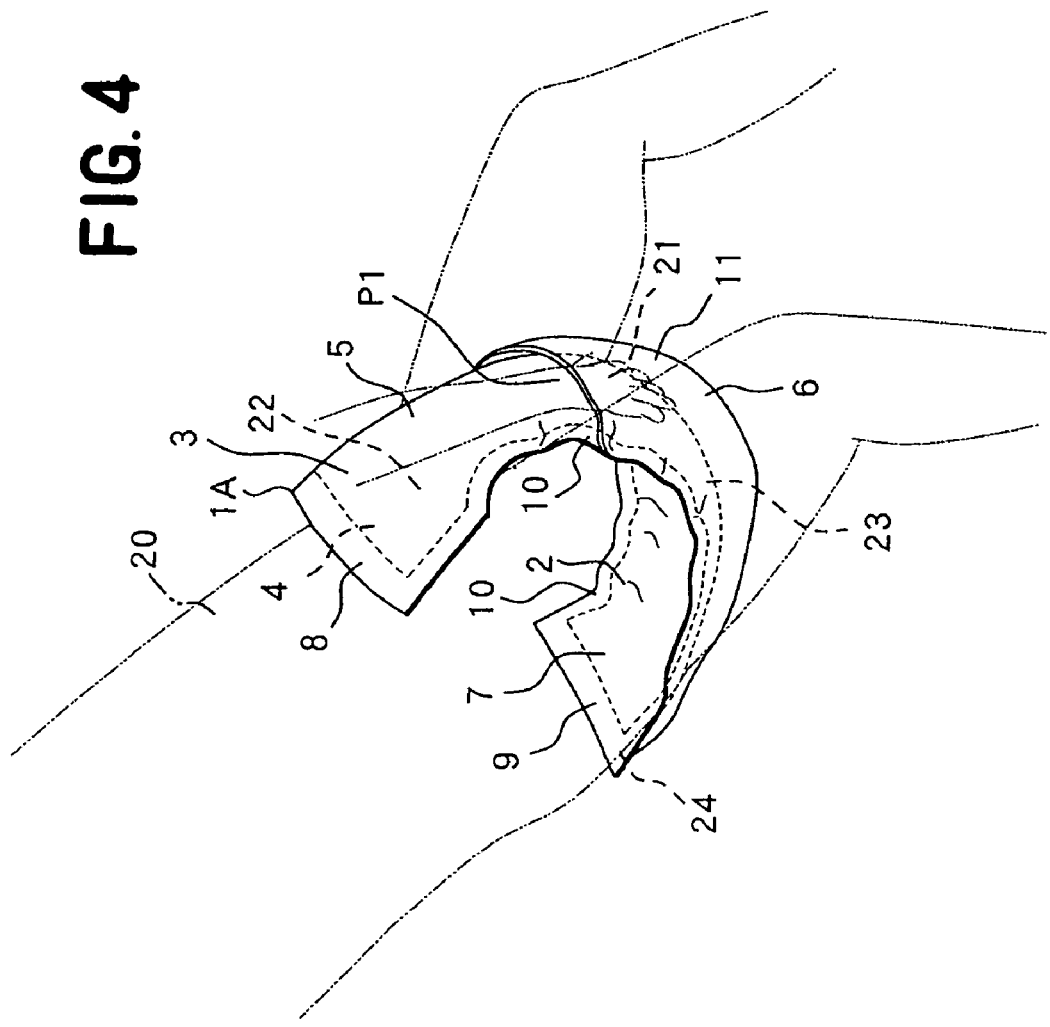
FIG. 4 is a perspective view showing the pad as put on the wearer's body.
Figure 5:
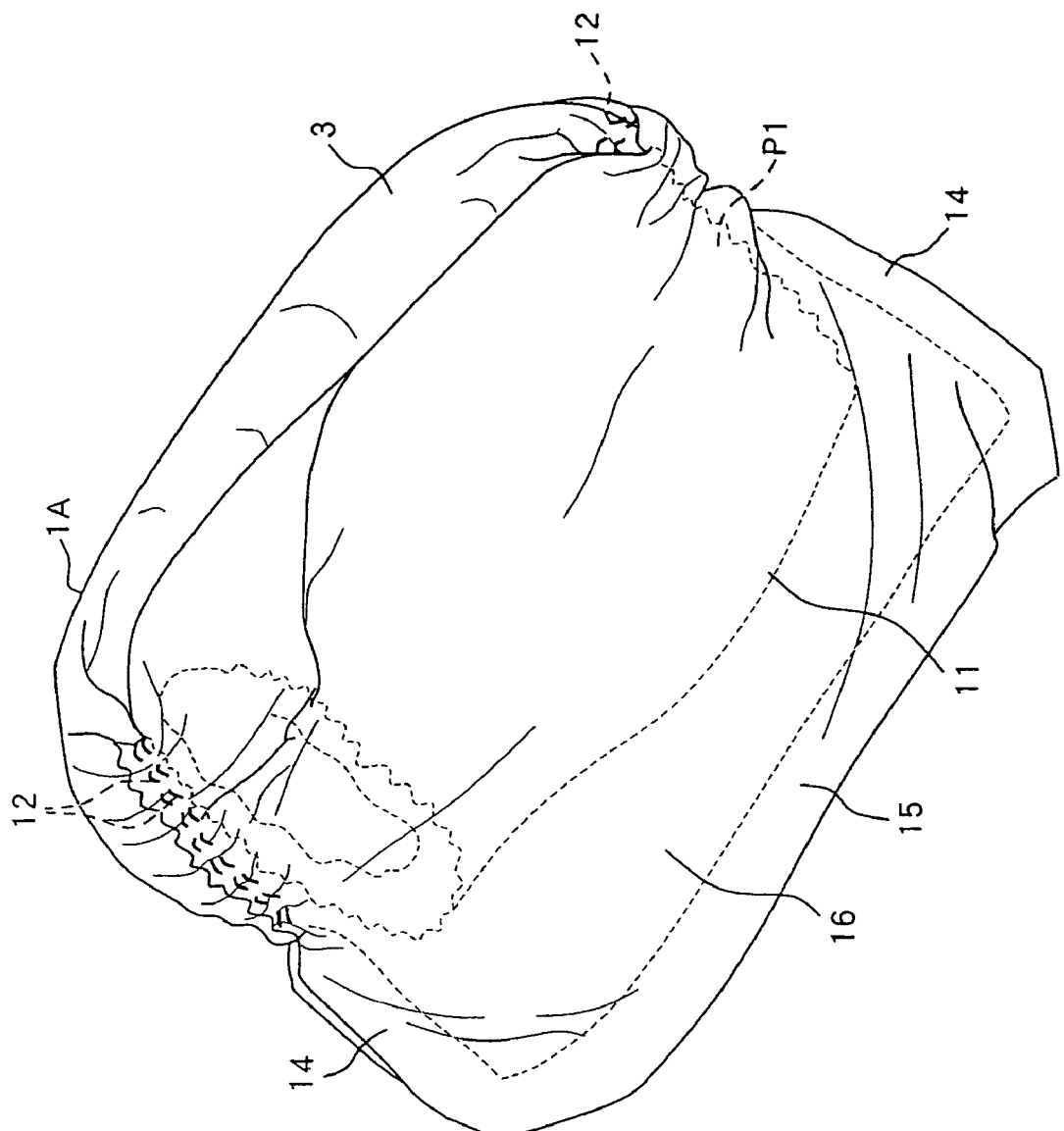
FIG. 5 is a perspective view showing the used pad as having been folded for disposal.

FIG. 4 is a perspective view showing the pad 1A as put on the wearer's body and FIG. 5 is a perspective view showing the used pad 1A as having been folded for disposal. In FIG. 4, the wearer 20 of the pad 1A is indicated by chain double-dashed lines.

To wear the pad 1A, the wearer 20 inserts his or her hand 21 into the pocket P1 (insertion space) and places the topsheet 2 of the pad 1A against his or her body so that a crotch region 23 of the wearer 20 may be correctly covered with the intermediate region 6, as shown in FIG. 4. With the pad 1A properly put on the wearer 20, the front region 5 faces a belly side 22 of the wearer 20, the rear region 7 faces a hip side 24 of the wearer 20 and the intermediate region 6 faces the crotch region 23 of the wearer 20. With the pad 1A put on the wearer 20 in this manner, the wearer 20 may discharge urine onto the topsheet 2 without anxiety. Urine is absorbed through the topsheet 2 in the core 4 and retained therein.

The pad 1A is adapted to be placed by its wearer 20 him- or herself against his or her body and thereby to place the pad 1A correctly against the urethral openings and vicinity thereof This ensures urine to be reliably absorbed by the pad 1A. Furthermore, it is not likely that the pad 1A once having been placed against the wearer's body might unintentionally fall off from the crotch region 23 of the wearer 20 because the wearer 20 can insert his or her hand 21 into the pocket P1 and thereby hold the pad 1A.

The pad 1A is distinguished from the conventional pad in that it is unnecessary to use shorts serving to hold the pad 1A in close contact with the wearer's body but the pad 1A can be placed against the wearer's body merely by inserting the wearer's hand into the pocket P1. In this way, the pad 1A can be easily used without any other separate holding means.

In the pad 1A, the cover sheet 11 is colored differently from the top- and backsheets 2, 3 and provided with illustration of rabbit's head printed thereon. Such a unique arrangement facilitates the wearer 20 to identify the surface to be placed against the wearer's body (topsheet 2) and to recognize the presence of the pocket P1.

For disposal of the used pad 1A, the pad 1A is longitudinally folded from the front region 5 toward the rear region 7, then the cover sheet 11 is reversed so that its inner surface may be exposed outward and the pad 1A folded in this manner is crammed into the pocket P1. The used pad 1A is maintained by the pocket 1A in its folded state and be thrown away in such a folded state.

Figure 6:
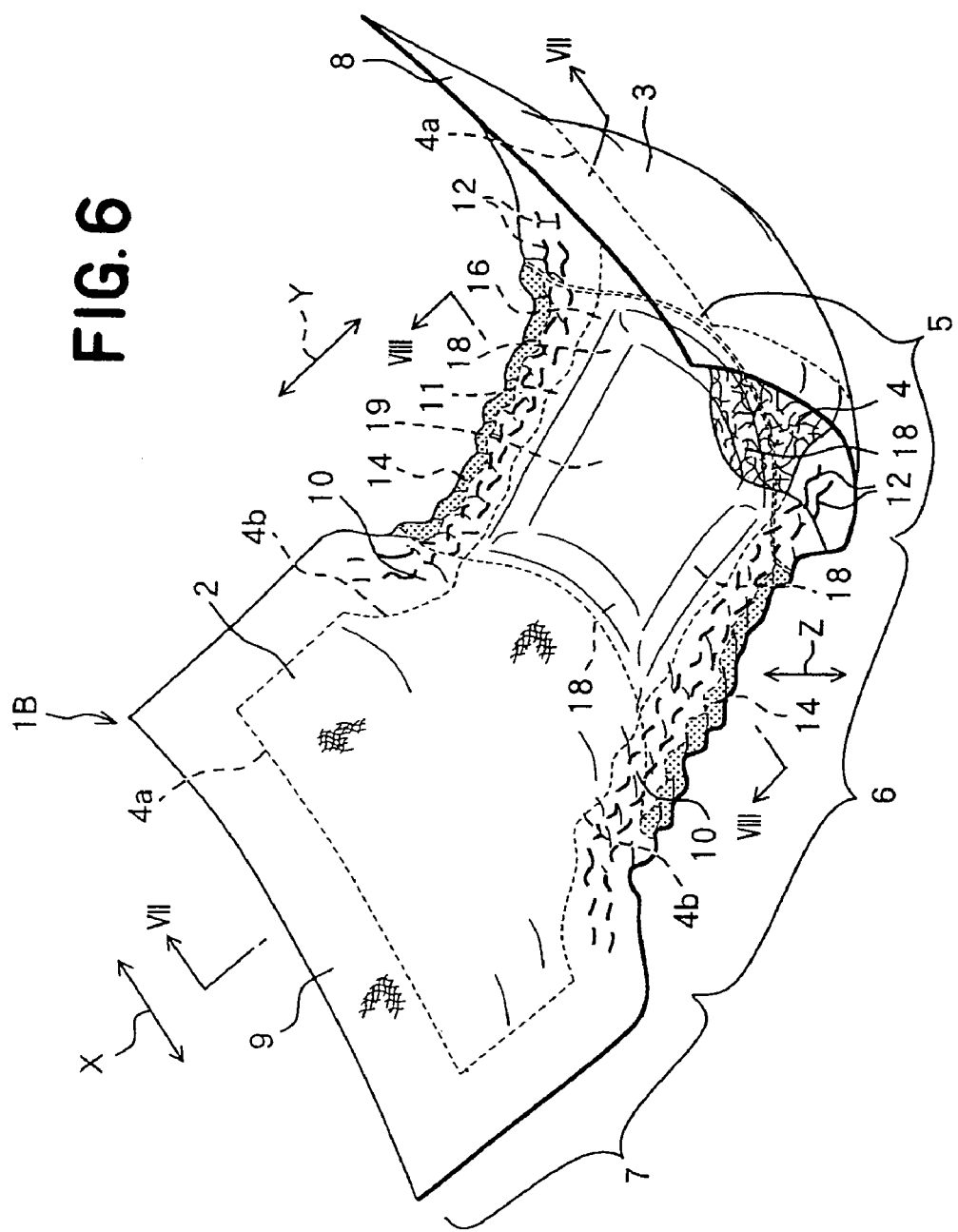
FIG. 6 is a partially cutaway perspective view showing another embodiment of the body fluid absorbent pad according to the invention.
Figure 7:
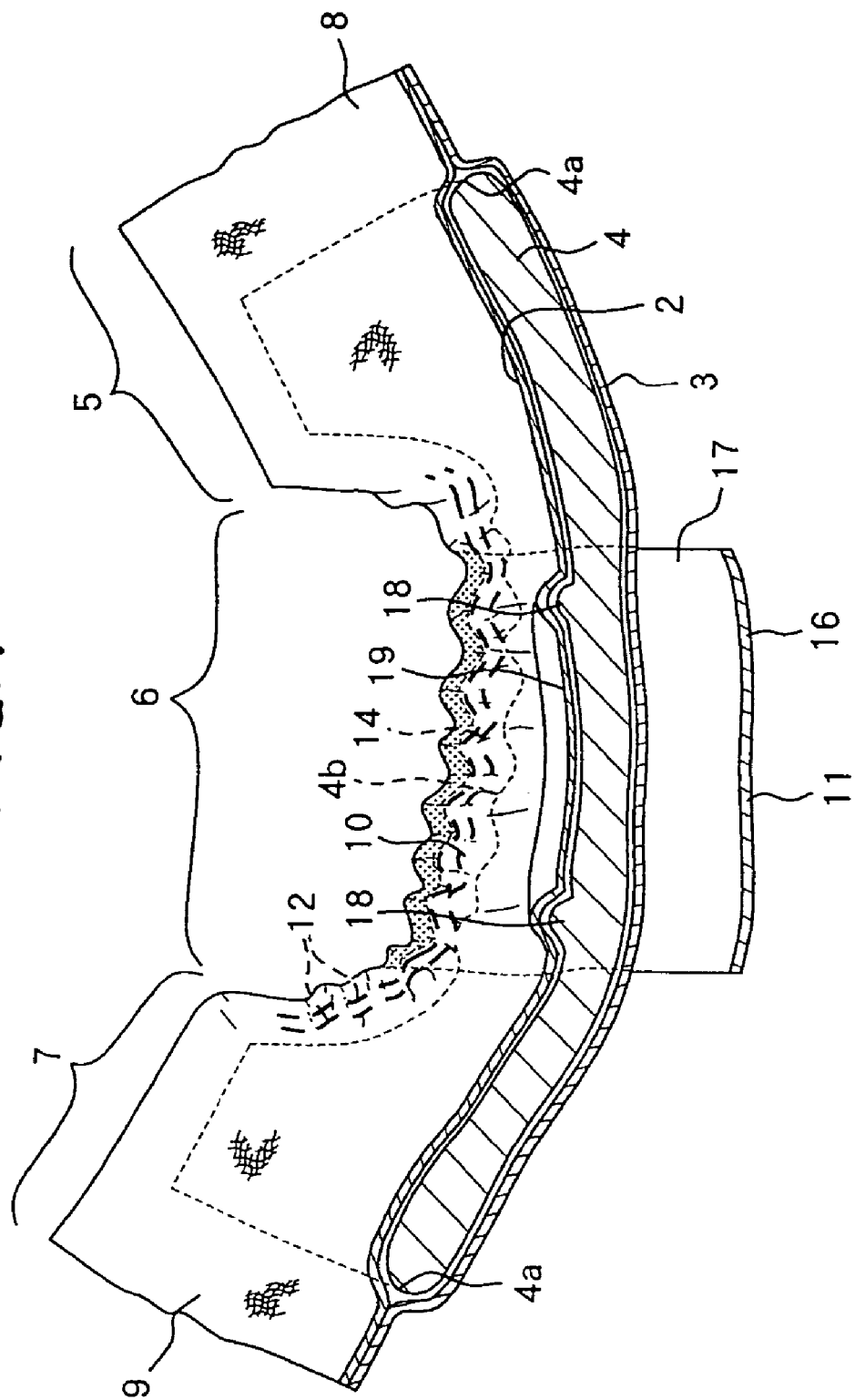
FIG. 7 is a sectional view taken along a line VII-VII in FIG. 6.
Figure 8:
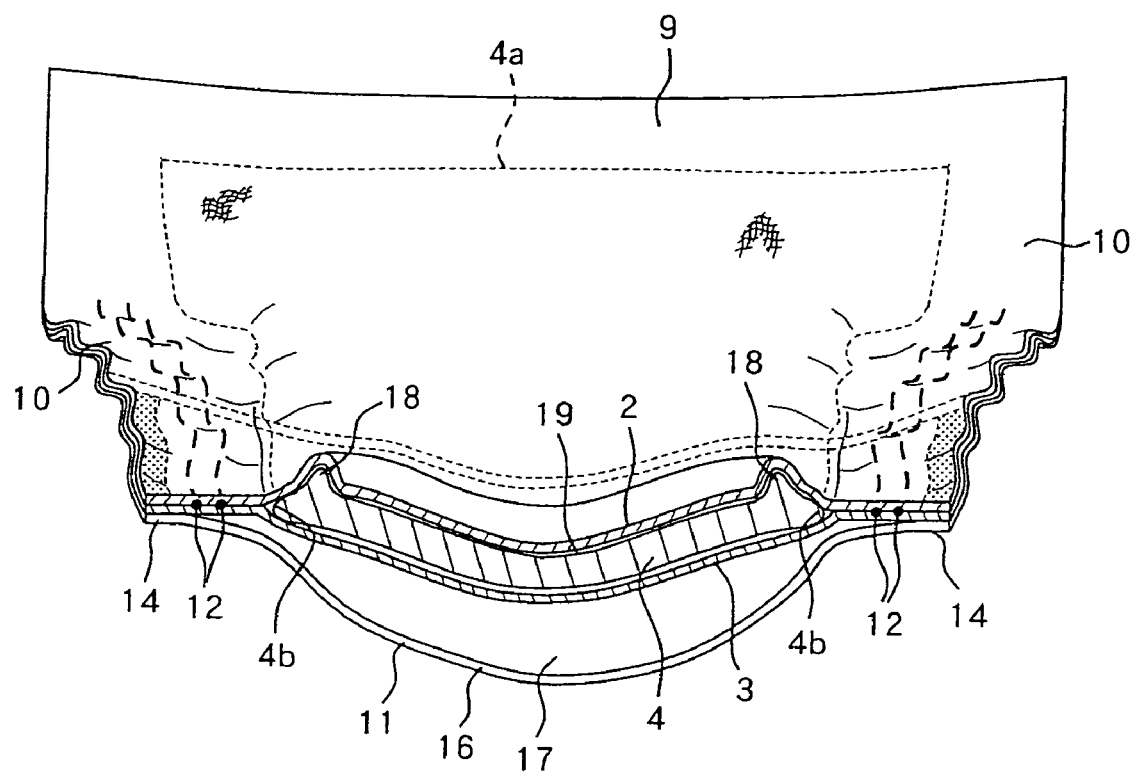
FIG. 8 is a sectional view taken along a line VIII-VIII in FIG. 6.

FIG. 6 is a partially cutaway perspective view showing a body fluid absorbent pad 1B according to a second embodiment of the invention, FIG. 7 is a sectional view taken along a line VII-VII in FIG. 6 and FIG. 8 is a sectional view taken along a line VIII-VIII in FIG. 6. The second embodiment of the present invention is illustrated by the pad in FIGS. 6-8 where component similar to those previously described have the same reference numeral.

The pad 1B comprises a liquid-pervious topsheet 2 facing the wearer's body, a liquid-impervious backsheet 3 facing away from the wearer's body and a liquid-absorbent core 4 interposed between the top- and backsheets 2, 3. The pad 1B defines, in the longitudinal direction, a front region 5, a rear region 7 and an intermediate region 6 extending between the front and rear regions 5, 7. The pad 1B is contoured by front and rear end portions 8, 9 lying outside longitudinally opposite ends 4a of the core 4 so as to extend in the transverse direction and transversely opposite side edge portions 10 lying outside transversely opposite side edges 4b of the core 4 so as to extend in the longitudinal direction.

The pad 1B includes the cover sheet 11 lying outside the backsheet 3 and thereby covers the outer surface of the sheet 3. The intermediate region 6 is provided with a plurality of elastically stretchable members 12 which are attached to the side edges 10 in a stretched state so as to extend in the longitudinal direction. These elastic members 12 are interposed between the top- and backsheets 2, 3 and secured to the respective inner surfaces of these sheets 2, 3. In FIG. 6, the pad 1B is curved in the longitudinal direction with the topsheet 2 inside as the elastic members 12 contract inward in the longitudinal direction. The core 4 is similar to that shown in FIG. 1 and extends between the front and rear regions 5, 7 of the pad 1B and is secured to respective inner surfaces of the top- and backsheets 2, 3.

The cover sheet 11 extends over the intermediate region 6. The cover sheet 11 is formed by substantially elastically stretchable hydrophobic fibrous nonwoven fabric. It should be understood that the cover sheet 11 may extend entirely over the front region 5, the intermediate region 6 and the rear region 7 and at least over the intermediate region 6. The cover sheet 11 is colored in the same color tone as the top- and backsheets 2, 3.

The cover sheet 11 has transversely opposite fixed side edge portions 14 secured to the side edge portions 10 of the pad 1B and a free portion 16 extending between the fixed side edge portions 14. Along the fixed side edge portions 14, the inner surface of the cover sheet 11 is secured to the outer surface of the backsheet 3. The free portion 16 is not secured to the backsheet 3 and let free therefrom. Between the backsheet 3 and the free portion 16 of the cover sheet 11, an insertion space 17 having a sufficient large volume into which a wearer 20 of the pad 1B can insert his or her hand 21 (See FIGS. 7 and 8).

The fixed side edge portions 14 of the cover sheet 11 are secured to the backsheet 3 in an unstretched state in the transverse direction. Alternatively, it is possible to secure the fixed side edge portions 14 of the cover sheet 11 to the backsheet 3 in a stretched state in the transverse direction.

Within a region of the core 4 in which the cover sheet 11 lies, the core 4 is formed in the vicinity of the cover sheet's peripheral edge with a ridge 18 raised toward the topsheet 2. A thickness dimension of the core 4 between the top- and backsheets 2, 3 as measured in the raised ridge 18 is larger than a thickness dimension of the core 4 in the other portion. The raised ridge 18 has a substantially annular shape. To ensure that the thickness dimension of the core 4 as measured in the raised ridge 18 is larger than the thickness dimension of the core 4 as measured in the other portion, an amount of pulp, synthetic resin fiber and polymer used in the raised ridge 18 may be adjusted to be larger than an amount of these components used in the other portion.

Along the front and rear end portions 8, 9, the top- and backsheets 2, 3 are overlaid and joined together. Along the side edge portions 10, the top- and backsheets 2, 3 are overlaid and joined together.

To wear the pad 1B, the wearer 20 inserts his or her hand 21 into the insertion space 17 and places the topsheet 2 of the pad 1B against his or her body so that a crotch region 23 of the wearer 20 may be correctly covered with the intermediate region 6 in the same manner as in the case of FIG. 4. With the pad 1B properly put on the wearer 20, the front region 5 faces the belly side 22 of the wearer 20, the rear region 7 faces the hip side 24 of the wearer 20 and the intermediate region 6 faces the crotch region 23 of the wearer 20. With the pad 1B put on the wearer 20 in this manner, the wearer 20 may discharge urine onto the portion 19 surrounded by the raised ridge 18. Urine is absorbed through the topsheet 2 in the core 4 and retained therein. In the case of the pad 1B, the raised ridge 18 defines a urine barrier adapted to prevent urine discharged on the portion 19 from leaking sideways beyond the peripheral edge of the pad 1B.

The pad 1B is adapted to be placed by its wearer 20 him- or herself against his or her body and thereby to place the pad 1B correctly against the urethral openings and vicinity thereof. This ensures urine to be reliably absorbed by the pad 1B. Furthermore, it is not apprehended that the pad 1B once having been placed against the wearer's skin might unintentionally fall off from the crotch region 23 of the wearer 20 because the wearer 20 can insert his or her hand 21 into the pocket P1 and thereby hold the pad 1B.

It is unnecessary for the pad 1B to use shorts serving to hold the pad 1B in close contact with the wearer's body but the pad 1B can be placed against the wearer's body merely by inserting the wearer's hand 21 into the insertion space 17. In this way, the pad 1B can be easily used without any other separate holding means. The cover sheet 11 is formed by elastically stretchable fibrous nonwoven fabric so that the cover sheet 11 may appropriate tighten the hand 21 inserted into the insertion space 17 and prevent the hand 21 from unintentionally falling off from the insertion space 17.

For disposal of the used pad 1B, though not shown, the pad 1B is longitudinally folded from the front region 5 toward the rear region 7, then the cover sheet 11 is reversed so that its inner surface may be exposed outward and the pad 1B folded in this manner is crammed into the pocket P1. The used pad 1B is maintained by the pocket 1B in its folded state and be thrown away in such folded state.

Figure 9:
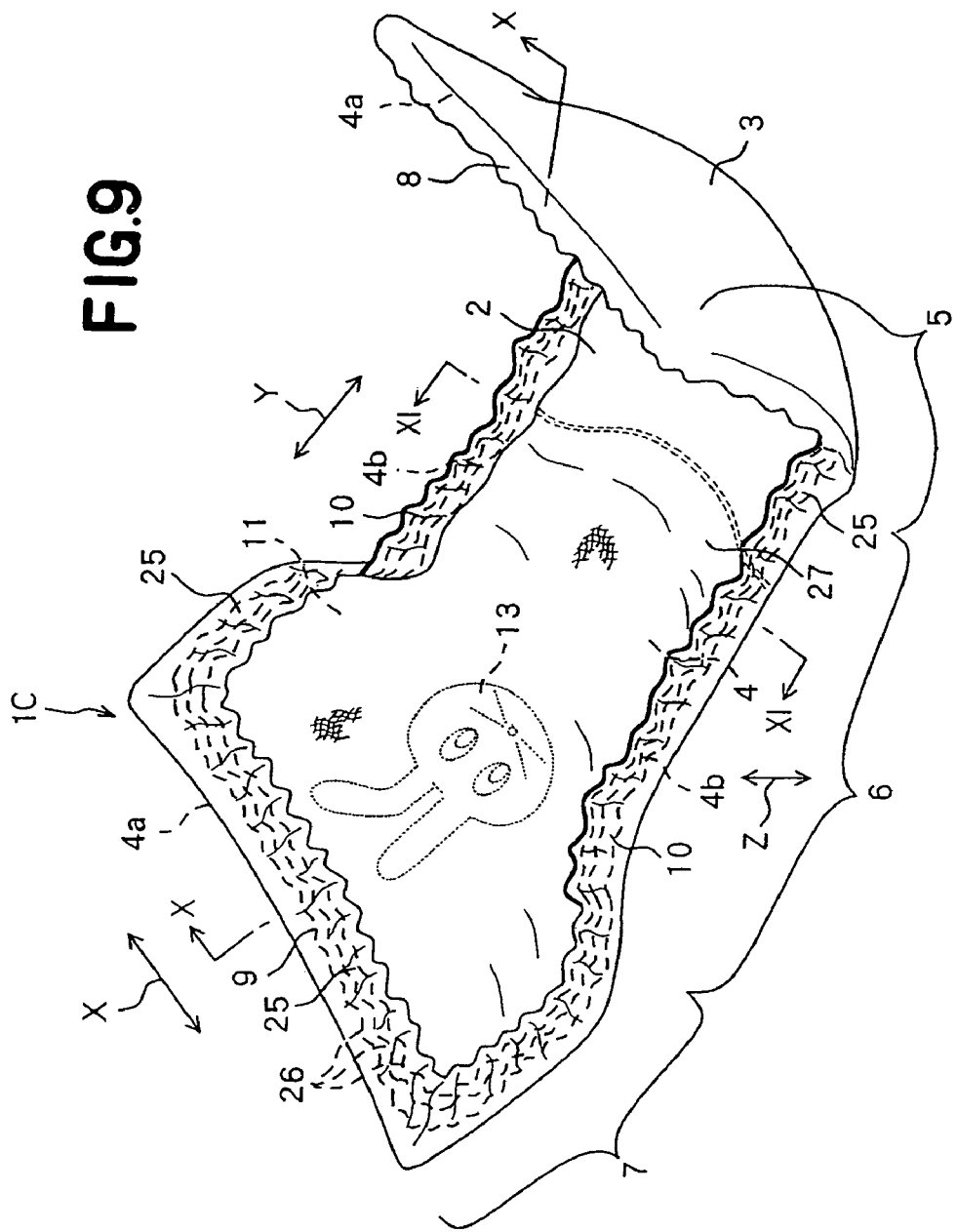
FIG. 9 is a perspective view showing still another embodiment of the body fluid absorbent pad according to the invention.
Figure 10:
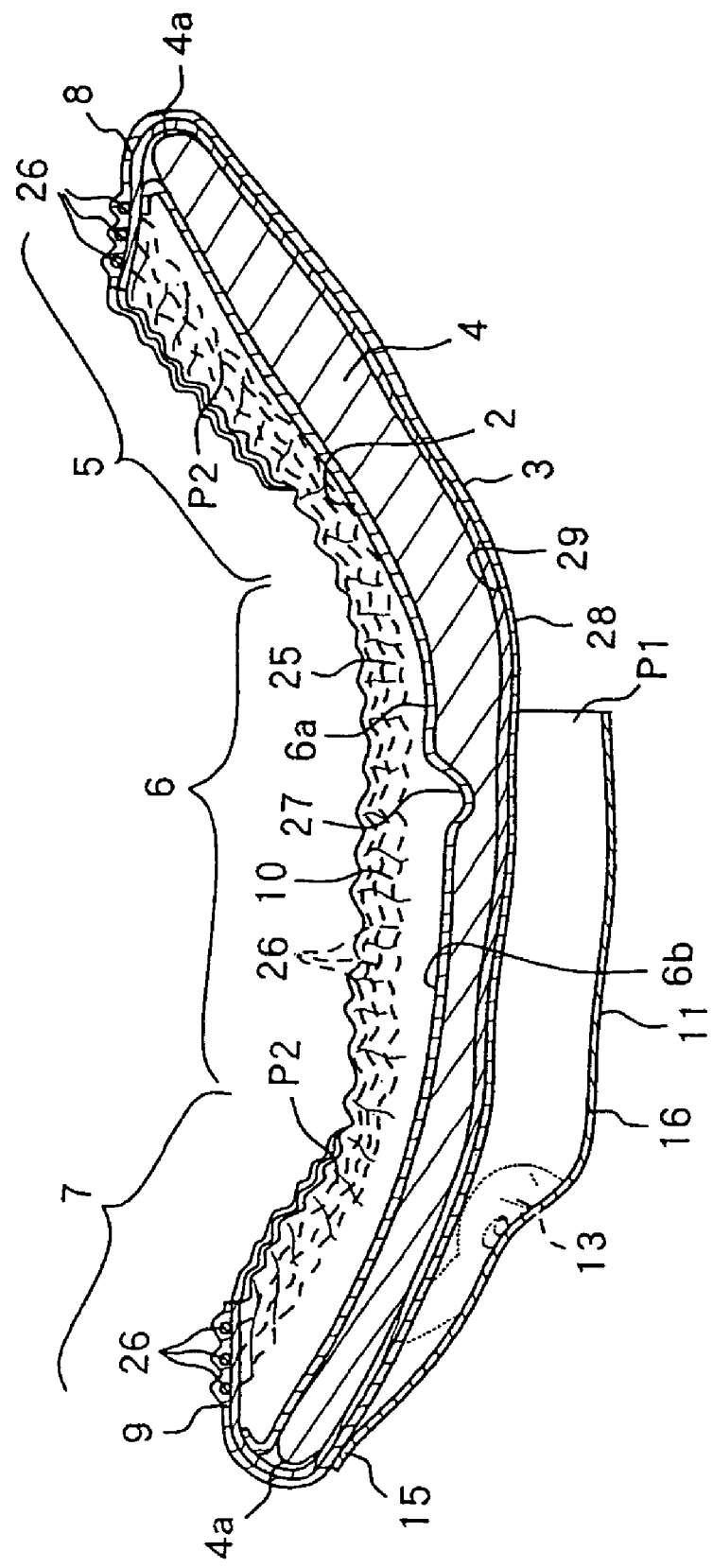
FIG. 10 is a sectional view taken along a line X-X in FIG. 9.
Figure 11:
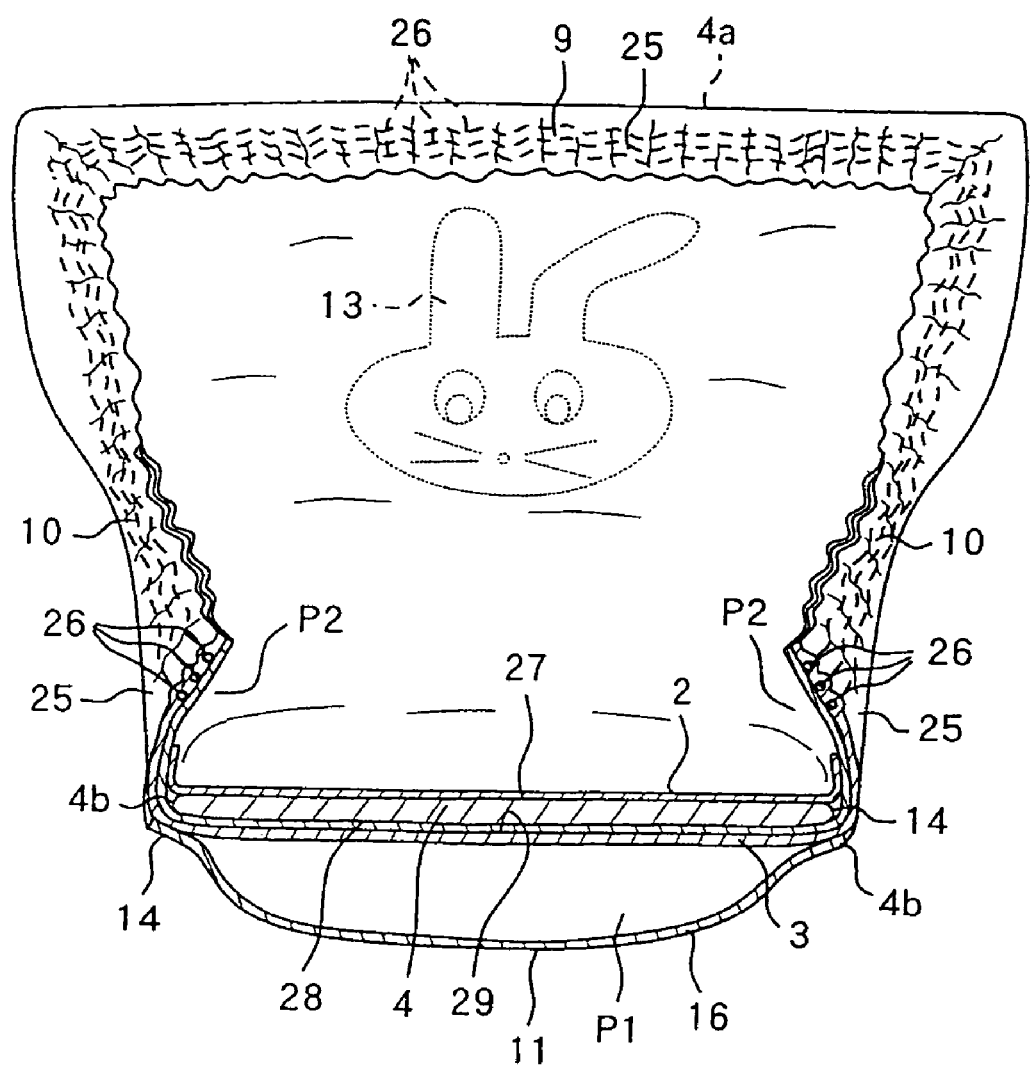
FIG. 11 is a sectional view taken along a line XI-XI in FIG. 9.

FIG. 9 is a perspective view showing a body fluid absorbent pad according to third embodiment of the invention, FIG. 10 is a sectional view taken along a line X-X in FIG. 9 and FIG. 11 is a sectional view taken along a line XI-XI in FIG. 9. The third embodiment of the present invention is illustrated by the pad in FIGS. 9-11 where component similar to those previously described have the same reference numeral.

The pad 1C comprises a liquid-pervious topsheet 2, a liquid-impervious backsheet 3 and a liquid-absorbent core 4 interposed between the top- and backsheets 2, 3. The pad 1C defines, in the longitudinal direction, a front region 5, a rear region 7 and an intermediate region 6 extending between the front and rear regions 5, 7. The pad 1C is contoured by front and rear end portions 8, 9 lying outside longitudinally opposite ends 4a of the core 4 so as to extend in the transverse direction and transversely opposite side edge portions 10 lying outside transversely opposite side edges 4b of the core 4 so as to extend in the longitudinal direction.

The pad 1C includes the cover sheet 11 covering outside the backsheet 3. The core 4 is similar to that shown in FIG. 1 and extends between the front and rear regions 5, 7 of the pad 1B and is attached to respective inner surfaces of the top- and backsheets 2, 3. The backsheet 3 is formed by a composite sheet consisting of a hydrophobic fibrous non-woven fabric 28 and a breathable but liquid-impervious plastic film 29 laminated with each other.

The cover sheet 11 extends over the intermediate region 6 and further over the rear region 7 to the rear end portion 9 of the pad 1A. The cover sheet 11 is formed by substantially non-stretchable hydrophobic fibrous nonwoven fabric. The cover sheet 11 is colored differently from the top- and backsheets 2, 3 (coloration is not shown). The cover sheet 11 has an illustration of rabbit's head printed on the outer surface of the cover sheet 11.

The cover sheet 11 has transversely opposite fixed side edge portions 14 extending in the longitudinal direction along the side edge portions 10 of the pad 1C, a fixed end portion 15 extending in the transverse direction along the rear end portion 9 of the pad 1C and a free portion 16 extending between these fixed side edge portions 14 and the fixed end portion 15. The fixed side edge portions 14 are secured to the core 4 in the vicinity of the side edges 4b of the core 4. The fixed end portion 15 is secured to the core 4 in the vicinity of the ends 4a of the core 4. Along the fixed side edge portions 14 and the fixed end portion 15, the inner surface of the cover sheet 11 is secured to the outer surface of the backsheet 3. The free portion 16 is not secured to the backsheet 3 and let free therefrom. Between the backsheet 3 and the free portion 16 of the cover sheet 11, a pocket P1 (insertion space) opening from the side of the front region 5 toward the side of the rear region 7 is defined (See FIGS. 10 and 11).

Along the front and rear end portions 8, 9 the top- and backsheets 2, 3 are overlaid and joined together. The top- and backsheets 2, 3 are folded inward at the front and rear end portions 8, 9 along the longitudinally opposite ends 4a of the core 4 in the longitudinal direction. These front and rear end portions 8, 9 are primarily defined by the backsheet 3. More specifically, longitudinally opposite ends of the backsheet 3 lie inward in the longitudinal direction rather than longitudinal opposite ends of the topsheet 2.

Along the side edge portions 10, the top- and backsheets 2, 3 are overlaid and joined together. The top- and backsheets 2, 3 are folded inward at the side edge portions 10 along the side edges 4b of the core 4 in the transverse direction. Most of the side edge portions 10 are formed by portions of the backsheet 3. Transversely opposite side edges of the backsheet 3 lie inward in the transverse direction rather than transversely opposite side edges of the topsheet 2.

The front and rear end portions 8, 9 as well as the side edge portions 10 are raised above the core 4 so as to form a peripheral wall 25 surrounding the core 4. The peripheral wall 25 is provided with a plurality of substantially annular elastically stretchable members 26 so as to be contractible in the longitudinal direction of these elastic members 26. These elastic members 26 are spaced apart from one another by given dimensions as viewed from the vicinity of the outermost circumference toward the vicinity of the innermost circumference of the peripheral wall 25 and attached to the peripheral wall 25 while these elastic members 26 are stretched at a predetermined ratio. The elastic members 26 are interposed between the nonwoven fabric 28 forming the backsheet 3 and the film 29 and secured to these nonwoven fabric 28 and film 29. The peripheral wall 25 is constricted inward in its circumferential direction above the core 4 as the elastic members 26 contract. Between the peripheral edge of the core 4 and the peripheral wall 25, a pocket P2 opening inward as viewed in the circumferential direction of the pad 1C.

A thickness dimension of the core 4 in the front region 5 and a front half 6a of the intermediate region 6 is larger than that in a rear half 6b of the intermediate region 6 as well as in the rear region 7, in other words, the core 4 bulge in the front region 5 and the front half 6a of the intermediate region 6. To adjust the thickness dimension in the front region 5 and the front half 6a of the intermediate region 6 to be larger than that in the rear half 6b of the intermediate region 6 as well as in the rear region 7, an amount of mixture consisting of pulp, synthetic resin fiber and polymer forming the core 4 in the front region 5 and the front half 6a of the intermediate region 6 may be larger than that in the rear half 6b of the intermediate region 6 as well as in the rear region 7. Regarding the density, the core 4 preferably has a density higher in the front region 5 and the front half 6a of the intermediate region 6 than that in the rear half 6b of the intermediate region 6 as well as in the rear region 7. To adjust the density of the core 4 in the front region 5 and the front half 6a of the intermediate region 6 to be higher than that in the rear half 6b of the intermediate region 6 as well as in the rear region 7, a density of mixture consisting of pulp, synthetic resin fiber and polymer forming the core 4 in the front region 6 and the front half 6a of the intermediate region 6 may be higher than that in the rear half 6b of the intermediate region 6 as well as in the rear region 7.

The pad 1C is formed in the intermediate region 6 with a folding guide 27 for folding the pad 1C in two in the longitudinal direction with the top sheet 2 inside. The folding guide 27 extends across a longitudinally middle zone of the intermediate region 6 in the transverse direction. Along the folding guide 27 in the intermediate region 6, the core 4 has a thickness dimension smaller than that in the other zone and stiffness lower than that in the other zone. Regarding the density, the core 4 may have a density either equal to or lower than a density in the other zone of the intermediate region 6. To adjust the density of the core 4 in the folding guide 27 to be lower than the density of the core 4 in the other zone of the intermediate region 6, a density of the mixture consisting of pulp, synthetic resin fiber and polymer forming the core 4 may be adjusted to be lower in the folding guide 27 than the other zone of the intermediate region 6.

Figure 12:
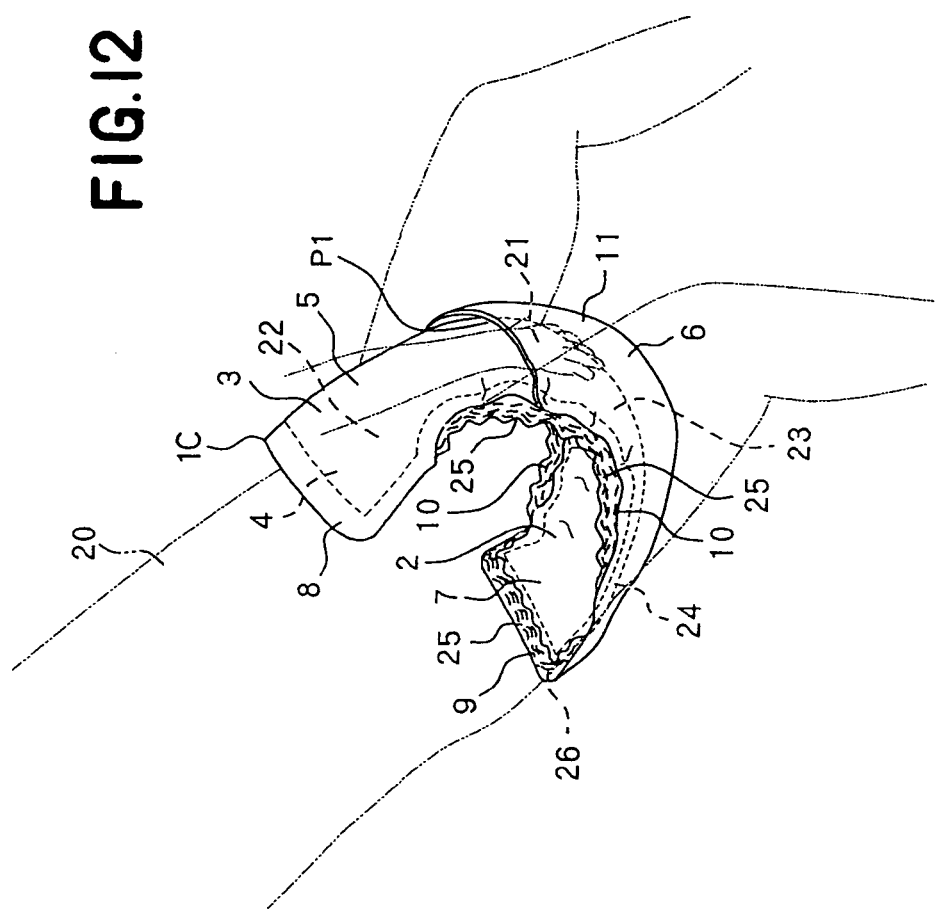
FIG. 12 is a perspective view showing the pad as put on the wearer's body.

FIG. 12 is a perspective view showing the pad 1C as put on the wearer's body. To wear the pad 1C, the wearer 20 inserts his or her hand 21 into the pocket P1 (insertion space) and places the topsheet 2 of the pad 1C against his or her body so that a crotch region 23 of the wearer 20 may be correctly covered with the intermediate region 6. Preparation for disposal of the used pad 1C is same as in the case of the pad 1A shown in FIG. 1 and the description of this preparation is not repeated here.

With the pad 1C properly put on the wearer 20, the front region 5 faces a belly side 22 of the wearer 20, the rear region 7 faces a hip side 24 of the wearer 20 and the intermediate region 6 faces the crotch region 23 of the wearer 20. With the pad 1C put on the wearer 20 in this manner, the wearer 20 may discharge urine onto the pad 1C. Urine is absorbed through the topsheet 2 in the core 4 and retained therein. In the case of this embodiment, the pad 1C is folded in two along the folding guide 27 in the longitudinal direction as the pad 1C is put on the wearer 20, so the front region 5 and the rear region 7 can be easily placed closely against the belly side 22 and the hip side 24 of the wearer 20, respectively. For disposal also, the pad 1C can be easily folded along the folding guide 27.

The pad 1C is adapted to be placed by its wearer 20 himor herself against his or her body and thereby to place the pad 1C correctly against the urethral openings and vicinity thereof. This ensures urine to be reliably absorbed by the pad 1C. Furthermore, it is not likely that the pad 1C once having been placed against the wearer's body might unintentionally fall off from the crotch region 23 of the wearer 20 because the wearer 20 can insert his or her hand 21 into the pocket P1 and thereby hold the pad 1C.

It is unnecessary for the pad 1C to use pants serving to hold the pad 1C in close contact with the wearer's body but the pad 1C can be placed against the wearer's body merely by inserting the wearer's hand into the pocket P1. In this way, the pad 1C can be easily used without any other separate holding means. In the pad 1C, the cover sheet 11 is colored differently from the top- and backsheets 2, 3 and provided with illustration of rabbit's head printed thereon. Such unique arrangement facilitates the wearer 20 to identify the surface to be placed against the wearer's body (topsheet 2) and to recognize the presence of the pocket P1.

In the pad 1C, the pocket P2 is formed between the peripheral edge of the core 4 and the peripheral wall 25, which is adapted to receive urine even if urine spreads on the outer surface of the topsheet 2 and reaches the peripheral edge of the core 4. Therefore, there is no anxiety that urine might leak beyond the front and rear end portions 8, 9 as well as beyond the side edge portions 10 of the pad 1C. Furthermore, the core 4 extending over the front region 5 and the front half 6a of the intermediate region 6 has the prominence dimension (thickness dimension) as measured upward from the surface of the core 4 facing the wearer's body which is larger than the prominence dimension as measured upward from the surface of the core 4 facing the wearer's body in the rear half 6b of the intermediate region 6 as well as in the rear region 7 of the core 4. With such unique arrangement, the front region 5 and the front half 6a of the intermediate region 6 can reliably absorb discharged urine even if a relatively large amount of urine is discharged.

Figure 13:
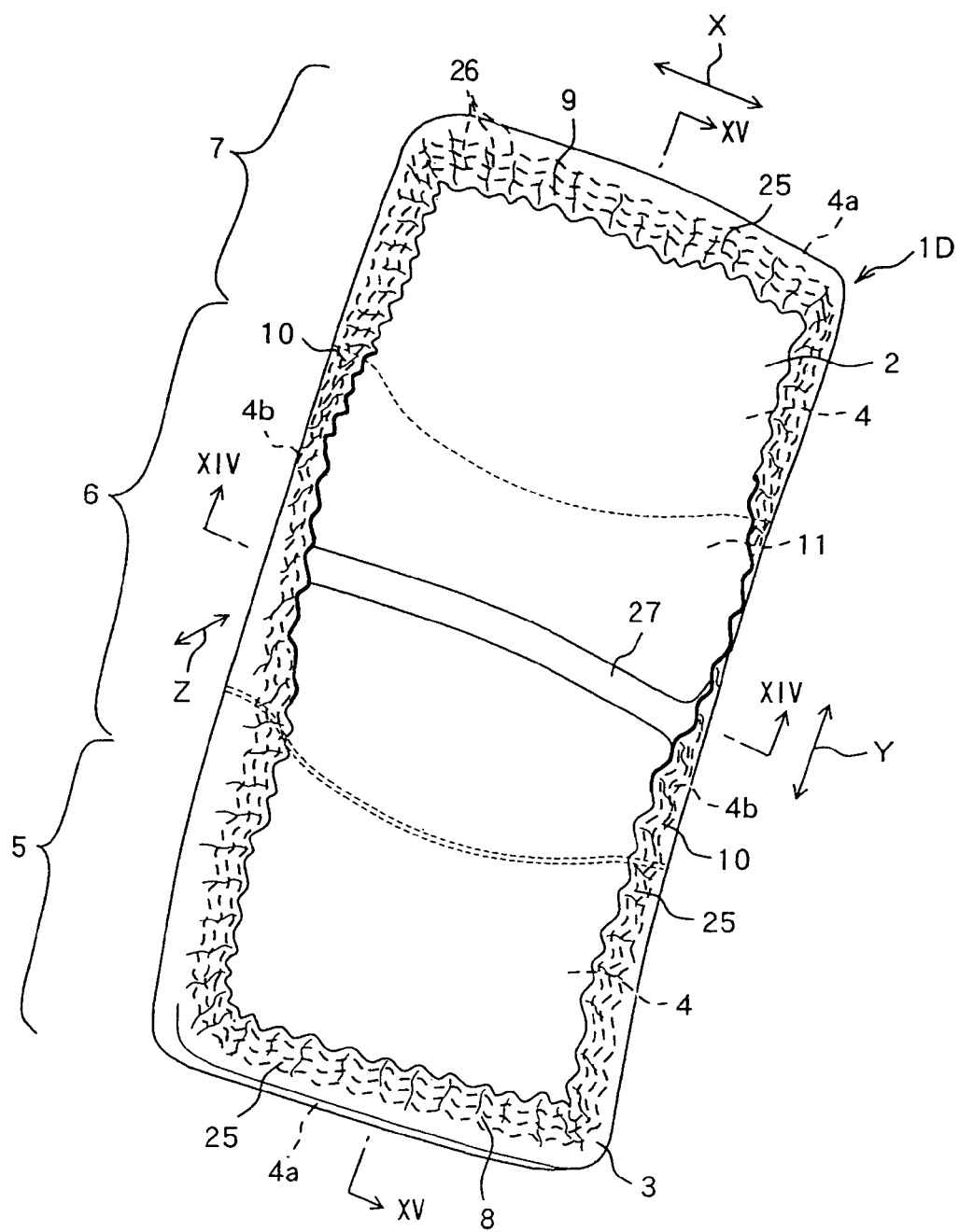
FIG. 13 is a perspective view showing further another embodiment of the body fluid absorbent pad according to the invention.
Figure 14:
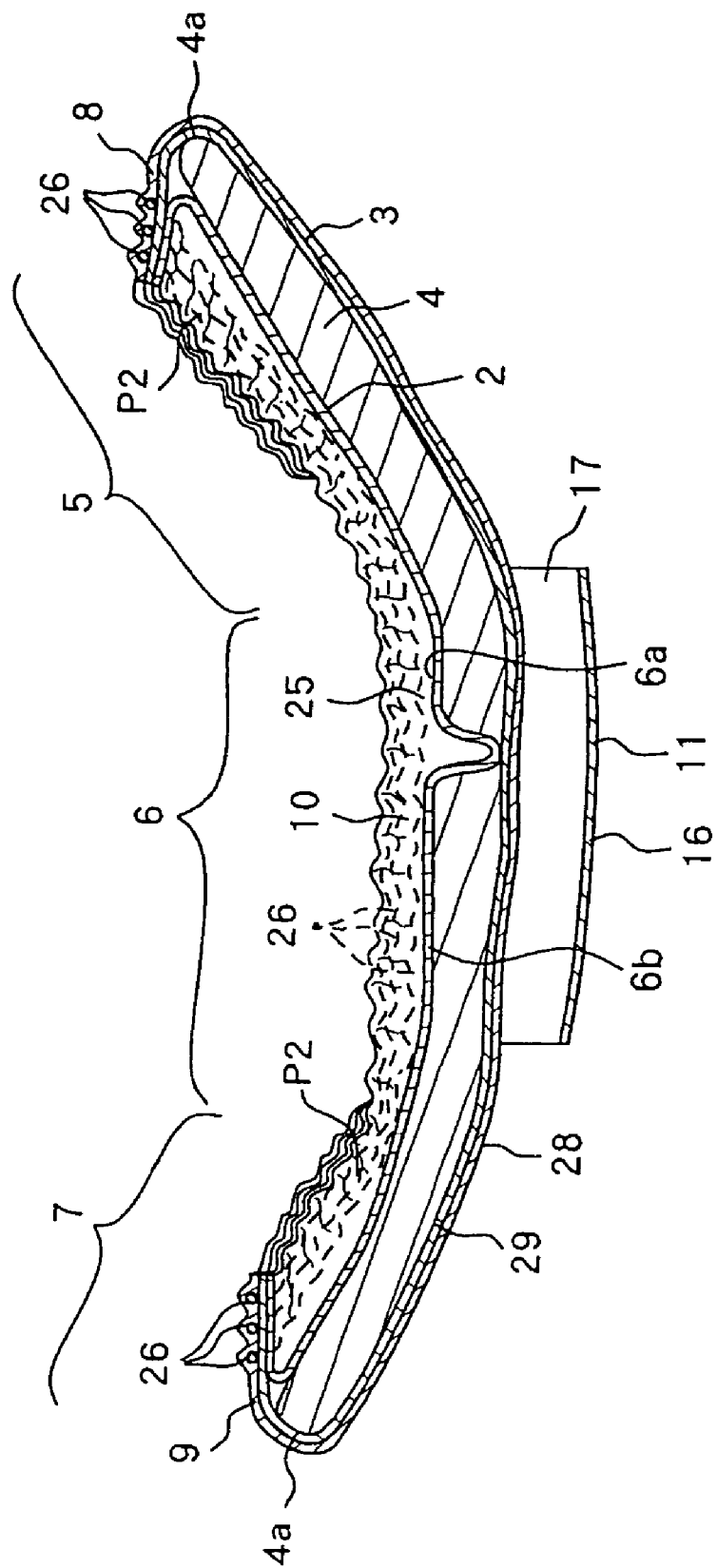
FIG. 14 is a sectional view taken along a line XIV-XIV in FIG. 13.
Figure 15:
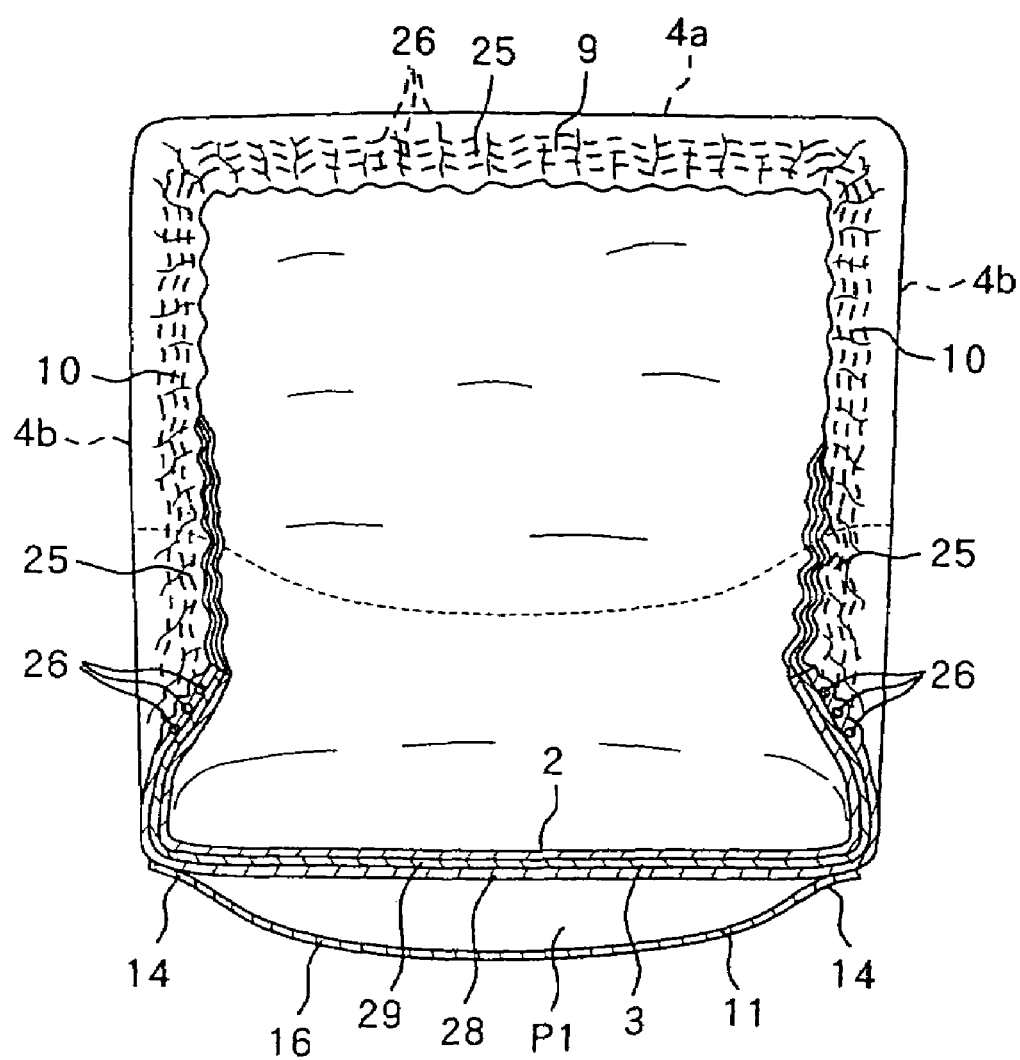
FIG. 15 is a sectional view taken along a line XV-XV in FIG. 13.

FIG. 13 is a perspective view showing a body fluid absorbent pad 1D according to fourth embodiment of the invention, FIG. 14 is a sectional view taken along a line XIV-XIV in FIG. 13 and FIG. 15 is a sectional view taken along a line XV-XV in FIG. 13. The fourth embodiment of the present invention is illustrated by the pad in FIGS. 13-15 where component similar to those previously described have the same reference numeral.

The pad 1D comprises a liquid-pervious topsheet 2 facing the wearer's body, a liquid-impervious backsheet 3 facing away from the wearer's body and the liquid-absorbent core 4 interposed between the top- and backsheets 2, 3. The pad 1D defines, in the longitudinal direction, a front region 5, a rear region 7 and an intermediate region 6 extending between the front and rear regions 5, 7. The pad 1D is contoured by front and rear end portions 8, 9 lying outside longitudinally opposite ends 4a of the core 4 so as to extend in the transverse direction and transversely opposite side edge portions 10 lying outside transversely opposite side edges 4b of the core so as to extend in the longitudinal direction.

The pad 1D includes the cover sheet 11 covering outside the backsheet 3. The core 4 is similar to that shown in FIG. 1 and extends between the front and rear regions 5, 7 of the pad 1D and is attached to respective inner surfaces of the top- and backsheets 2, 3. The backsheet 3 is formed by a composite sheet consisting of a hydrophobic fibrous nonwoven fabric 28 and breathable but liquid-impervious plastic film 29 laminated with each other.

The cover sheet 11 extends over the intermediate region 6. The cover sheet 11 is formed by elastically stretchable hydrophobic fibrous nonwoven fabric. The cover sheet 11 is colored in the same color tone as the top- and backsheets 2, 3. The cover sheet 11 has transversely opposite fixed side edge portions 14 extending along the side edge portions 10 of the pad 1D in the longitudinal direction and a free portion 16 extending between these fixed side edge portions 14. The fixed side edge portions 14 are secured to the core 4 in the vicinity of the side edges 4b. In the fixed side edge portions 14, the inner surface of the cover sheet 11 is secured to the outer surface of the backsheet 3. The free portion 16 is not secured to the backsheet 3 and let free therefrom. Between the backsheet 3 and the free portion 16 of the cover sheet 11, an insertion space 17 having a sufficient large volume into which a wearer 20 of the pad 1D can insert his or her hand 21 (See FIGS. 14 and 15).

The front and rear end portions 8, 9 of the pad 1D extend inward beyond the opposite ends 4a of the core 4 in the longitudinal direction. These front and rear end the portions 8, 9 are defined by respective portions of the top- and backsheets 2, 3 extending inward beyond the opposite ends 4a of the core 4 in the longitudinal direction. Along these front and rear end portions 8, 9, the top- and backsheets 2, 3 are overlaid and joined together.

The side edge portions 10 of the pad 1D are defined by respective portions of the top- and backsheets 2, 3 extending inward beyond the transversely opposite ends 4b of the core 4 in the in the transverse direction. Along these side edge portions 10, the top- and backsheets 2, 3 are overlaid and joined together.

The front and rear end portions 8, 9 as well as the side edge portions 10 of the pad 1D are raised above the core 4 so as to form a peripheral wall 25 surrounding the core 4. The peripheral wall 25 is provided with a plurality of substantially annular elastically stretchable members 26 so as to be contractible in the longitudinal direction of these elastic members 26. These elastic members 26 are spaced apart one from another by given dimensions as viewed from the vicinity of the outermost circumference toward the vicinity of the innermost circumference of the peripheral wall 25 and attached to the peripheral wall 25 while these elastic members 26 are stretched at a predetermined ratio. The elastic members 26 are interposed between the nonwoven fabric 28 forming the backsheet 3 and the film 29 and secured to these nonwoven fabric 28 and film 29. The peripheral wall 25 is constricted inward in its circumferential direction above the core 4 as the elastic members 26 contract. Between the peripheral edge of the core 4 and the peripheral wall 25, a pocket P2 opening inward as viewed in the circumferential direction of the pad 1D.

The intermediate region 6 is formed with a folding guide 27 along which the pad 1D can be folded in two in the longitudinal direction with the topsheet 2 inside. The folding guide 27 extends across a longitudinally middle zone of the intermediate region 6 in the transverse direction and formed by the top- and backsheets 2, 3 having not the core 4 therebetween. Along the folding guide 27, the respective inner surfaces of these top- and backsheets 2, 3 may be secured to each other or let free from each other. The core 4 is not present along the folding guide 27, so stiffness of the pad 1D is lower in the folding guide 27 than in the other zone of the pad 1D.

To wear the pad 1D, the wearer 20 inserts his or her hand 21 into the insertion space 17 and places the topsheet 2 of the pad 1D against his or her skin so that a crotch region 23 of the wearer 20 may be correctly covered with the intermediate region 6, in the same manner as the manner shown in FIG. 12. The procedure for disposal of the used pad 1D is similar to the procedure having been described in reference with FIG. 6 and detailed description is not repeated here.

With the pad 1D properly put on the wearer 20, the front region 5 faces a belly side 22 of the wearer 20, the rear region 7 faces a hip side 24 of the wearer 20 and the intermediate region 6 faces the crotch region 23 of the wearer 20. With the pad 1D put on the wearer 20 in this manner, the wearer 20 may discharge urine onto the pad 1D. Urine is absorbed through the topsheet 2 in the core 4 and retained therein. In the case of this embodiment, the pad 1D is folded along the folding guide 27 in two in the longitudinal direction as the pad 1D is put on the wearer 20, so the front region 5 and the rear region 7 can be easily placed closely against the belly side 22 and the hip side 24 of the wearer 20, respectively. For disposal also, the pad 1D can be easily folded along the folding guide 27.

The pad 1D is adapted to be placed by its wearer 20 himor herself against his or her body and thereby to place the pad 1D correctly against the urethral openings and vicinity thereof. This ensures urine to be reliably absorbed by the pad 1D. Furthermore, it is not likely that the pad 1D once having been placed against the wearer's body might unintentionally fall off from the crotch region 23 of the wearer 20 because the wearer 20 can insert his or her hand 21 into the insertion space 17 and thereby hold the pad 1D.

It is unnecessary for the pad 1D to use shorts serving to hold the pad 1D in close contact with the wearer's body but the pad 1D can be placed against the wearer's body merely by inserting the wearer's hand into the insertion space 17. In this way, the pad 1D can be easily used without any other separate holding means. In the pad 1D, the pocket P2 is formed between the peripheral edge of the core 4 and the peripheral wall 25, which is adapted to receive urine even if urine spreads on the outer surface of the topsheet 2 and reaches the peripheral edge of the core 4. Therefore, there is no anxiety that urine might leak beyond the front and rear end portions 8, 9 as well as beyond the side edge portions 10 of the pad 1D.

A stock material for the topsheet 2 may be selected from the group consisting of a hydrophilic fibrous nonwoven fabric, a hydrophobic fibrous nonwoven fabric having a plurality of perforations and a plastic film having a plurality of fine perforations. A stock material for the backsheet 3 of the pad 1A, 1B may be selected from the group consisting of a hydrophobic fibrous nonwoven fabric, a breathable but liquid-impervious plastic film, a composite nonwoven fabric comprising a two or more hydrophobic fibrous nonwoven fabric layers laminated one on another and a composite sheet comprising a hydrophobic fibrous nonwoven fabric and a breathable but liquid-impervious plastic film laminated on each other. A stock material for the backsheet 3 of the pad 1C, 1D may be selected from a group consisting of hydrophobic fibrous nonwoven fabric, breathable but liquid-impervious plastic film and composite nonwoven fabric comprising two or more hydrophobic fibrous nonwoven fabric layers laminated one on another. Nonwoven fabric used to implement the invention may be selected from the group consisting of products obtained by spun lace-, needle punch-, melt blown-, thermal bond-, spun bond- and chemical bond-processes. A stock material for the cover sheet 11 may be selected from the group consisting of a hydrophilic fibrous nonwoven fabric, a breathable but liquid-impervious plastic film and a stretchable plastic film.

It is also possible to use, as a stock material for the backsheet 3 and the cover sheet 11, a composite nonwoven fabric comprising melt blown fibrous nonwoven fabric having a high water-resistance and spun bond fibrous nonwoven fabric having high strength and high flexibility laminated on at least one surface of the former (SM nonwoven fabric or SMS nonwoven fabric).

The hydrophilic fibrous nonwoven fabric can be made from any one of synthetic fibers, semi-synthetic fibers and regenerated fibers, all modified to become hydrophilic, or conjugated fibers comprising a mixture thereof. While not limited, the synthetic fiber may be selected from the group consisting of polyester-, polyacrylonitrile-, polyvinyl chloride-, polyethylene-, polypropylene- and polystyrene-based fibers. It is also possible to use, as the synthetic fibers, any one of core-and-sheath-type conjugated fibers, side-by-side-type conjugated fibers, modified hollow fibers, microporous fibers and bond-type conjugated fibers. The hydrophobic fibrous nonwoven fabric can be made from synthetic fibers. The hydrophobic fibrous nonwoven fabric may contain semi-synthetic fibers and/or regenerated fibers both treated to become water-repellent.

The elastically stretchable fibrous nonwoven fabric may be of melt blown- or spun bond-type. As component fibers of the elastically stretchable nonwoven fabric, stretchable fibers obtained by melt-spinning thermoplastic elastomer resin. It is also possible to use, as the elastically stretchable fibrous nonwoven fabric, a composite nonwoven fabric comprising elastically stretchable hydrophobic fibrous nonwoven fabric made of thermoplastic elastomer resin fibers and hydrophobic fibrous nonwoven fabric made of crimped fibers obtained by melt-spinning thermoplastic synthetic resin laminated on at least one surface of the former fibrous nonwoven fabric.

The super-absorbent polymer may be selected from the group consisting of starch-based polymer, cellulose-based polymer and synthetic polymer. The super-absorbent polymer may be granular or fibrous.

Joining the top- and backsheets 2, 3, securing the cover sheet 11 to the backsheet 3, securing the core 4 to the top- and backsheets 2, 3 and securing the elastic members 12, 26 to the top- and backsheets 2, 3 may be carried out using an adhesive or welding means such as heat-sealing or sonic sealing. The adhesive may be selected from the group consisting of a hot melt adhesive, a polyacrylate adhesive or a rubber adhesive. Preferably, the adhesive is applied on the respective inner surfaces of the top- and backsheets 2, 3 in spiral, zigzag, dotted or striped pattern.

Also in the pad 1A shown in FIG. 1, the region of the core 4 overlying the cover sheet 11 may be formed with the ridge 17 similar to that shown in FIG. 6 which extends along the peripheral edge of the cover sheet 11 and protrudes toward the topsheet 2. In the pads 1A, 1C shown in FIGS. 1 and 9, respectively, it is possible to form the cover sheet 11 using an elastically stretchable fibrous nonwoven fabric. In the pads 1A, 1B shown in FIGS. 1 and 6, respectively, it is possible to form the intermediate region 6 with the folding guide 27 extending across the transversely middle zone. For the pads 1C, 1D shown in FIGS. 9 and 13, respectively, it is not essential to form the intermediate region 6 with the folding guide 27.

In the pads 1B, 1D shown in FIGS. 6 and 13, respectively, it is possible to color the cover sheet 11 differently from coloration of the top- and backsheets 2, 3 and its is also possible to provide the cover sheet 11 with the indicator element 13 such as an illustration, letters, patterns or symbols. Each of the pads 1B, 1D may have the cover sheet 11 colored and formed with the indicator element 13 in such manner to facilitates the wearer 20 to identify the surface to be placed against the wearer's body (topsheet 2) and to recognize the presence of the insertion space 17.

It is possible to arrange the pad 1D shown in FIG. 13 in the manner similar to that shown in FIG. 9 so that the thickness dimension of the core 4 in the front region 5 and the front half 6a of the intermediate region 6 is larger than that in the rear half 6b of the intermediate region 6 as well as in the rear region 7 and the prominence dimension of the core 4 as measure upward from the surface of the core 4 facing the wearer's body in the front region 5 and the front half 6a of the intermediate region 6 is larger than that in the rear half 6b of the intermediate region 6 as well as in the rear region 6.

The pad according to the invention is primarily characterized in that the wearer him- or herself may insert his or her hand into the insertion space (pocket) to place the pad against his or her body and thereby to place the pad correctly against the urethral openings and vicinity thereof. This ensures urine to be reliably absorbed by the pad. Furthermore, it is not likely that the pad once having been placed against the wearer's body might unintentionally fall off from the wearer's crotch region because the wearer can insert his or her hand into the insertion space and thereby hold the pad.

This pad is distinguished from the conventional pad in that it is unnecessary to use shorts serving to hold the pad in close contact with the wearer's body but the pad can be placed against the wearer's body merely by inserting the wearer's hand into the insertion space. In this way, the pad can be easily used without any other separate holding means.

In the case of the pad having the elastically stretchable peripheral wall surrounding the core, the pocket is formed between the peripheral edge of the core and the peripheral wall, which is adapted to receive urine even if urine spreads on the outer surface of the topsheet and reaches the peripheral edge of the core.

With the pad in which the core has its prominence dimension (thickness dimension) as measured upward from the surface of the core facing the wearer's body in the front region and the front half of the intermediate region larger than that in the rear half of the intermediate region as well as in the rear region of the core, the front region and the front half of the intermediate region can reliably absorb discharged urine even if a relatively large amount of urine is discharged and prevent urine from flowing into the rear half of the intermediate region and the rear region.

In the case of the pad formed with the folding guide extending across the intermediate region, the pad is folded in two along the folding guide in the longitudinal direction as the pad is put on the wearer, so the front region and the rear region can be easily placed closely against the belly side and the hip side of the wearer, respectively. For disposal also, the pad can be easily folded along the folding guide.

With the pad in which the core is formed along the peripheral edge of the cover sheet with the raised ridge, this raised ridge defines a urine barrier adapted to prevent urine discharged onto the pad from leaking sideways beyond the peripheral edge of the pad.

With the pad in which the cover sheet is colored differently from the top- and backsheets and provided with an illustration of rabbit's head printed thereon, the wearer can easily identify the surface to be placed against his or her body and recognize the presence of the insertion space (pocket).

What is claimed is:

1. A disposable body fluid absorbent pad having a longitudinal direction and a transverse direction, said pad further comprising:
   a front region;
   a rear region;

an intermediate region between said front region and said rear region;
a liquid-pervious topsheet;
a liquid-impervious backsheet;
a liquid-absorbent core between said liquid-pervious topsheet and said liquid-impervious backsheet;
said pad being contoured by longitudinally opposite end portions extending in said transverse direction outside longitudinal front and rear ends of said liquid-absorbent core and transversely opposite side edge portions extending in said longitudinal direction outside transversely opposite side edges of said liquid absorbent core; and
an insertion space means comprising a cover sheet which overlaps at least a portion of said liquid-impervious backsheet so as to define an insertion space between said cover sheet and a part of an outer surface of said liquid-impervious backsheet and at least one non-sealable opening to guide a wearer's hand into said insertion space and along the outer surface of said liquid-impervious backsheet, with at least a part of a periphery of said cover sheet joined onto an outer surface of said liquid-impervious backsheet,
wherein said longitudinally front and rear end portions of said pad extend inward in said longitudinal direction from said longitudinally front and rear opposite ends of said liquid-absorbent core so as to lie above said liquid-absorbent core while said side edge portions of said pad extend inward in said transverse direction from said opposite side edge portions of said pad so as to lie above said liquid-absorbent core and said longitudinally front and rear end portions cooperate with said side edge portions to form a peripheral wall adapted to surround said liquid-absorbent core.

2. The pad according to claim 1, wherein said peripheral wall is provided with elastically stretchable members attached thereto so that said elastically stretchable members substantially describe loops in a circumferential direction of said peripheral wall and are contractible in said circumferential direction.

3. The pad according to claim 1, wherein a prominence dimension of said liquid-absorbent core measured upward from a surface of said core facing a wearer's body in said front region and a front half of said intermediate region is larger than that in a rear half of said intermediate region and said rear region.

4. The pad according to claim 1, wherein said intermediate region is formed with a folding guide extending across said intermediate region in said transverse direction along which said pad is folded in two with said topsheet inside and said liquid-absorbent core has a stiffness lower in said folding guide than in said other zone of said liquid-absorbent core.

5. The pad according to claim 1, wherein said intermediate region is formed with a folding guide extending across said intermediate region in said transverse direction along which said pad is folded in two with said topsheet inside and said folding guide is formed by said top- and backsheets except for said liquid-absorbent core.

6. The pad according to claim 1, wherein said liquid-absorbent core is formed in a vicinity of a peripheral edge of said cover sheet with a raised ridge and said liquid-absorbent core has a thickness dimension measured between said top- and backsheets is larger in said raised ridge than in the other zone of said liquid-absorbent core except for said raised ridge.

* * * * *